(12) United States Patent
Dayton et al.

(10) Patent No.: US 10,787,625 B2
(45) Date of Patent: Sep. 29, 2020

(54) PROCESS FOR EXTRACTION OF OIL FROM ALGAL BIOMASS

(71) Applicant: Bunge Global Innovation LLC, White Plains, NY (US)

(72) Inventors: Christopher L. G. Dayton, Jupiter, FL (US); Ellen Cristina de Mello Lazarini, São Paulo (BR); Jean Ricardo de Souza, Gaspar (BR); Karen Carvalho, São Paulo (BR); Eloisa Zanin Pytlowanciv, São José do Rio Preto (BR); Bruna Montalvão Lima Ferraz, São José do Rio Preto (BR)

(73) Assignee: Bunge Global Innovation LLC, White Plains, NY (US)

( * ) Notice: Subject to any disclaimer, the term of this patent is extended or adjusted under 35 U.S.C. 154(b) by 0 days.

(21) Appl. No.: 15/716,396

(22) Filed: Sep. 26, 2017

(65) Prior Publication Data

US 2019/0016988 A1    Jan. 17, 2019

Related U.S. Application Data

(60) Provisional application No. 62/531,814, filed on Jul. 12, 2017.

(51) Int. Cl.
| | | |
|---|---|---|
| *C12P 7/00* | (2006.01) | |
| *C11B 1/02* | (2006.01) | |
| *C11B 1/10* | (2006.01) | |
| *C12P 7/64* | (2006.01) | |

(52) U.S. Cl.
CPC ............... *C11B 1/025* (2013.01); *C11B 1/10* (2013.01); *C12P 7/6427* (2013.01); *C12Y 304/21* (2013.01); *C12Y 304/21062* (2013.01)

(58) Field of Classification Search
None
See application file for complete search history.

(56) References Cited

U.S. PATENT DOCUMENTS

| | | | |
|---|---|---|---|
| 5,130,242 A | 7/1992 | Barclay | |
| 5,340,594 A | 8/1994 | Barclay | |
| 5,407,957 A | 4/1995 | Kyle et al. | |
| 7,431,952 B2 * | 10/2008 | Bijl | A23D 9/00 424/780 |
| 9,101,151 B2 | 8/2015 | Kobzeff et al. | |
| 9,408,404 B2 | 8/2016 | Weaver et al. | |

FOREIGN PATENT DOCUMENTS

| | | |
|---|---|---|
| WO | 2006/046943 A2 | 5/2006 |
| WO | 2015/092544 A1 | 6/2015 |
| WO | 2015/092546 A1 | 6/2015 |

OTHER PUBLICATIONS

Barrett et al. (Peptide & Protein Colloquium, 638th Meeting, Reading University, Apr. 1991, pp. 707-715).*
Chabrand et al. (Enzyme & Microbial Technol., vol. 45, 2009, pp. 28-35).*
Gerken et al., "Enzymatic cell wall degradation of Chlorella vulgaris and other microalgae for biofuels production," Planta. 237(1):239-253 (2013) (Epub Sep. 26, 2012).
Ledesma-Amaro, "Microbial oils: A customizable feedstock through metabolic engineering," Eur. J. Lipid Sci. Technol. 116:0000-0000 (2014).
Winwood, "Recent developments in the commercial production of DHA and EPA rich oils from micro-algae," OCL 20(6) D604 (2013).
United States Patent and Trademark Before the Patent Trial and Appeal Board, Ex parte Dragomir Nikolov, Alexander Pankov, and Jochen Wiedmann, Appeal No. 2013-000274, U.S. Appl. No. 12/314,706, Decision on Appeal mailed Mar. 27, 2015 (7 pages).
"Alcalase® Food Grade," Novozymes A/S, 5 pages (2002).
"Product catalog 2013, Immozymes, enzymes & Immobeadds," ChiralVision, pp. 1-21 (2013).
DSM, Japan, Catalog 24 pages (2016).
DSM, "Product specification sheet, Maxipro BAP," Jan. 25, 2019, 2 pages.

* cited by examiner

*Primary Examiner* — Hope A Robinson
(74) *Attorney, Agent, or Firm* — Jones Day

(57) ABSTRACT

Provided here is an enzymatic process for extraction of oil from algae biomass. The oils produced by the processes herein are used in animal feed and human consumption.

21 Claims, No Drawings

Specification includes a Sequence Listing.

PROCESS FOR EXTRACTION OF OIL FROM ALGAL BIOMASS

CROSS REFERENCE TO RELATED APPLICATION

This application claims the benefit of the priority of U.S. Provisional Application No. 62/531,814, filed Jul. 12, 2017, the disclosure of which is incorporated herein by reference in its entirety.

REFERENCE TO SEQUENCE LISTING SUBMITTED VIA EFS-WEB

This application was filed electronically via the USPTO EFS-WEB server, as authorized and set forth in MPEP § 1730 II.B.2.(a)(A), and this electronic filing includes an electronically submitted sequence (SEQ ID) listing; the entire content of this sequence listing is herein incorporated by reference for all purposes. The sequence listing is identified on the electronically filed .txt file as follows:

| File Name | Date of Creation | Size |
|---|---|---|
| 011631-0119-999_ST25.txt | Jan. 7, 2020 | 803 bytes |

FIELD

Provided herein is an enzymatic process for extraction of low saturate oils from an algae biomass. The enzymes used in the processes herein are endopeptidases, including serine endopeptidases enzymes. The oils produced by the processes herein may be used in animal feeds or further processed by refining, bleaching and deodorization for human consumption.

BACKGROUND

An oil high in polyunsaturated fatty acids obtained from algal biomass is useful in animal feeds or can be further processed by refining, bleaching and deodorization for human consumption. The existing methods for obtaining such oils from algal biomass involve drying the biomass after the fermentation. The drying process is very expensive and causes deterioration of the oil due to the presence of the heat in the drying process causing the sugars in the biomass to burn, darken, and oxidize of the oil. If the dried biomass is then mechanically pressed, the heat used in the press and the heat generated from the friction required to rupture the cells also causes the oil to darken and essentially become black. Additionally, pressing aids (hulls of soybean, rice or oat and wheat fiber) are used to increase the friction in the mechanical pressing in order to enhance the efficiency of the press. The pressing aids absorb some of the oil and may dilute the lipids by extraction some oil present in the hulls. An excellent mechanical pressing will leave approximately 8 to 10 percent oil in the pressed cake. To capture the remaining oil, the press cake is then solvent extracted to bring the residual oil in the biomass press cake to below 0.5 percent oil. The additional heating of the biomass press cake and desolventizing will cause additional darkening of the oil.

A process is needed to remove the oils from the algae biomass that prevents deterioration of the oil and darkening due to the Mallard reaction of the sugars in the conventional processes.

SUMMARY OF THE INVENTION

In certain embodiments, provided herein is a process for extracting of an oil high in polyunsaturated fatty acids from an algae biomass, wherein the process comprises contacting an algae fermentation broth with an endopeptidase enzyme, and extracting the oil high in polyunsaturated fatty acids. In certain embodiments, provided herein is a process for extracting of an oil high in polyunsaturated fatty acids from an algae biomass, wherein the process comprises contacting an algae fermentation broth with a serine endopeptidase enzyme, and extracting the oil high in polyunsaturated fatty acids.

In certain embodiments, the process provided herein recovers greater than about 60%, 70%, 80%, 85%, 90%, 95% or 99% oil high in polyunsaturated fatty acids from the algae biomass. The processes provided herein do not use surfactants, salts, aggressive chemicals, high temperatures, high pH, drying, and/or harsh mechanical treatment of the fermentation broth.

In one embodiment, the step of contacting the algae fermentation broth with an endopeptidase enzyme is conducted at a temperature of about 30° C. to about 80° C. and at a pH level of from about pH 6 to about pH 10. In one embodiment, the step of contacting the algae fermentation broth with a serine endopeptidase enzyme is conducted at a temperature of about 30° C. to about 80° C. and at a pH level of from about pH 6 to about pH 8.

In one embodiment, the step of contacting the algae fermentation broth with a serine endopeptidase enzyme is conducted at a temperature of about 30° C. to about 80° C. and at a pH level of from about pH 6 to about pH 10. In one embodiment, the step of contacting the algae fermentation broth with a serine endopeptidase enzyme is conducted at a temperature of about 30° C. to about 80° C. and at a pH level of from about pH 6 to about pH 8.

In one embodiment, the step of recovering the oil high in polyunsaturated fatty acids comprises extraction with a non-polar solvent, such as hexane.

In one embodiment, the oil obtained by the process provided herein comprises greater than 50%, 60%, 70% or 80% polyunsaturated fatty acids based on total weight of the oil.

In certain embodiments, the processes provided herein can be adapted for industrial scale extraction of the oil high in polyunsaturated fatty acids.

The oil obtained by the processes provided herein is used as an animal feed, or further processed by refining, bleaching and deodorization for human consumption.

DETAILED DESCRIPTION

Definitions

As used herein, the term "endopeptidase" refers to an enzyme that cleaves internal peptide bonds (nonterminal) in proteins.

As used herein, the term "serine endopeptidase" refers to an enzyme that cleaves peptide bonds in proteins, in which serine serves as the nucleophilic amino acid at the active site.

As used herein, the terms "broth" or "fermentation broth" or "algae fermentation broth" refer to the liquid obtained at the end of an aerobic microalgae bioprocess that includes the microalgae cells, products of fermentation, metabolites and the reminiscent nutrients and sugar.

As used herein, the term "algae biomass" to any cellular material derived from algae. The algae can be naturally occurring, or it can be genetically modified to enhance production of oils high in polyunsaturated fatty acid. In certain embodiments, the biomass is microalgae. The processes provided herein can be practiced with any microalgae. The microalgae can be grown in a closed system, such as a bioreactor, or it can be grown in open ponds. The microalgae can be grown with or without sunlight (autotrophically or heterotrophically) and with many varied carbon sources. The microalgae used herein can include any naturally occurring species or any genetically engineered microalgae. In certain embodiments, the microalgae is genetically engineered to have improved lipid production characteristics, including but not limited to optimizing lipid yield per unit volume and/or per unit time, carbon chain length, and the number of double or triple bonds. The microalgae can be grown in freshwater, brackish water, brines, or saltwater.

As used herein, the terms "polyunsaturated fatty acid" or "long chain polyunsaturated fatty acid", refer to an unsaturated fatty acid having a carbon chain length of at least 20. Such polyunsaturated fatty acid can have at least 2 or at least 3 double bonds. Exemplary polyunsaturated fatty acid include docosahexaenoic acid, docosapentaenoic acid, and/or arachidonic acid. Polyunsaturated fatty acids include free fatty acids and compounds comprising PUFA residues, including phospholipids; esters of fatty acids; triacylglycerols; diacylglycerides; monoacylglycerides; lysophospholipids; phosphatides; etc.

As used herein, the terms "oil high in polyunsaturated fatty acid" or "oil high in long chain polyunsaturated fatty acid", refer the oil obtained from the algae biomass and/or algae fermentation broth, wherein the oil comprises greater than about 50%, 60%, 70% or 80% polyunsaturated fatty acids based on total weight of the oil.

In certain embodiments, provided herein is a process for extracting an oil high in polyunsaturated fatty acids from an algae fermentation broth, wherein the process comprises contacting the broth with a serine endopeptidase enzyme and extracting the oil high in polyunsaturated fatty acids.

In one embodiment, the process comprises adjusting the pH of the broth to about 6 to 10. In one embodiment, the process comprises adjusting the pH of the broth to about 6 to 8. In one embodiment, the process comprises adjusting the pH to about 6, 6.5, 7, 7.5, 8, 8.5, 9, 9.5 or 10. In one embodiment, the process comprises adjusting the pH of the broth to about 6.5 to 7.5. In one embodiment, the process comprises adjusting the pH to about 6, 6.5, 7, 7.5 or 8. In one embodiment, the process comprises adjusting the pH to about 7.

In one embodiment, the pH of the broth is adjusted with a base such as sodium hydroxide or potassium hydroxide. In one embodiment the pH of the broth is adjusted with a dilute sodium hydroxide solution.

In one embodiment, the process comprises heating the broth to a temperature of about 30° C. to about 80° C. In one embodiment, the process comprises heating the broth to a temperature of about 40° C. to about 60° C. In one embodiment, the process comprises heating the broth to a temperature of about 30° C., 40° C., 45° C., 50° C., 60° C., 70° C. or 80° C. In one embodiment, the process comprises heating the broth to a temperature of about 50° C.

In certain embodiments, the broth is contacted with the serine endopeptidase enzyme for about 1-24 hours. In certain embodiments, the broth is contacted with the serine endopeptidase enzyme for about 5-20, 7-20, 7-15, 8-20, 9-20, 10-20, or 12-20 hours. In certain embodiments, the broth is contacted with the serine endopeptidase enzyme for 9-20, 10-20, or 12-20 hours. In certain embodiments, the broth is contacted with the serine endopeptidase enzyme for about 1, 3, 5, 7, 9, 11, 12, 13, 14, 15, 16, 17, 18, 19 or 20 hours.

In one embodiment, the extraction of the oil is conducted with a non-polar solvent such as hexane, pentane, heptane and octane. In one embodiment, the non-polar solvent comprises hexane. In one embodiment, the non-polar solvent is hexane.

In certain embodiments, the broth comprises a lipid-rich algae, including algae from the genus *Thraustochytrium*, *Schizochytrium* or mixtures thereof. In certain embodiments, the broth comprises an algae from the genus *Schizochytrium*. In certain embodiments, the broth comprises *Schizochytrium limacinum*.

In certain embodiments, the algae fermentation broth is obtained by processes known in art. Exemplary processes are described in U.S. Pat. Nos. 9,453,172; 9,023,625; 9,023,616 and 6,607,900. In certain embodiments, the algae fermentation broth comprises an algae density of from about 40 to about 300 g/L. In certain embodiments, the algae fermentation broth comprises an algae density of about 40-290 g/L, 40-280 g/L, 40-250 g/L, 40-200 g/L, 40-180 g/L, 40-150 g/L, 40-120 g/L, 40-100 g/L, or 40-80 g/L. In certain embodiments, the algae fermentation broth comprises an algae density of about 100-300 g/L, 100-290 g/L, 100-280 g/L, 100-250 g/L, 100-200 g/L, 100-180 g/L, or 100-150 g/L.

In certain embodiments, the algae biomass in the broth comprises about 30% to about 80% oil high in polyunsaturated fatty acids based on the total weight of the algae biomass. In certain embodiments, the algae biomass in the broth comprises about 40% to about 70% oil high in polyunsaturated fatty acids based on the total weight of the algae biomass. In certain embodiments, the algae biomass in the broth comprises about 50% to about 65% oil high in polyunsaturated fatty acids based on the total weight of the algae biomass. In certain embodiments, the algae biomass in the broth comprises about 40%, 45%, 50%, 55%, 57%, 60%, 65% or 70% oil high in polyunsaturated fatty acids based on the total weight of the algae biomass.

In certain embodiments, the endopeptidase used in the process herein is a serine endopeptidase enzyme. In certain embodiments, the serine endopeptidase enzyme used in the process provided herein is Alcalase®, Multifect® PR 6L, Maxipro® BAP or a mixture thereof. In one embodiment, the serine endopeptidase enzyme used in the process provided herein is Multifect® PR 6L. In one embodiment, the serine endopeptidase enzyme used in the process provided herein is Alcalase®. In another embodiment, the serine endopeptidase enzyme used in the process provided herein is Maxipro® BAP.

In certain embodiments, the process provided herein recovers greater than about 50% oil high in polyunsaturated fatty acids from the algae biomass based on the total amount of polyunsaturated fatty acid oil present in the algae biomass. In certain embodiments, the process provided herein recovers greater than about 60%, 70%, 80%, 85%, 90%, 95% or 99% oil high in polyunsaturated fatty acids from the algae biomass based on the total amount of polyunsaturated fatty acid oil present in the algae biomass. In certain embodiments, the process provided herein recovers about 50-100%, 60-100%, 70-100%, 80-100%, 85-100%, 90-100%, oil high in polyunsaturated fatty acids from the algae biomass based on the total amount of polyunsaturated fatty acid oil present in the algae biomass. In certain embodiments, the process provided herein recovers about 50-95%, 60-95%, 70-95%, 80-95%, 85-95%, 90-99%, oil high in polyunsaturated fatty acids from the algae biomass based on the total amount of polyunsaturated fatty acid oil present in the algae biomass.

In one embodiment, the oil obtained by the process provided herein comprises greater than 50%, 60%, 70% or 80% polyunsaturated fatty acids based on total weight of the oil. In one embodiment, the oil obtained by the process provided herein comprises about 50%-99%, about 50%-95%, about 50%-90%, about 50%-85%, about 50%-80% or about 50%-75% polyunsaturated fatty acids based on total weight of the oil. In one embodiment, the oil obtained by the process provided herein comprises about 60%-99%, about 60%-95%, about 60%-90%, about 60%-85%, about 60%-80% or about 60% to 75% polyunsaturated fatty acids based on total weight of the oil. In one embodiment, the oil obtained by the process provided herein comprises about 70%-99%, about 70%-95%, about 70%-90%, about 70%-85%, about 70%-80% or about 70% to 75% polyunsaturated fatty acids based on total weight of the oil. In one embodiment, the oil obtained by the process provided herein comprises about 60%, 70%, 80%, 85%, 90% or 95% polyunsaturated fatty acids based on total weight of the oil In one embodiment, the oil obtained by the process provided herein comprises about 45-65% docosahexaenoic acid (C22:6ω-3 or DHA) based on total weight of the oil. In one embodiment, the oil obtained by the process provided herein comprises about 50-60% docosahexaenoic acid (C22:6ω-3 or DHA) based on total weight of the oil.

In one embodiment, the oil obtained by the process provided herein comprises about 10-25% docosapentaenoic acid (C22:5ω6 or DPA) based on total weight of the oil. In one embodiment, the oil obtained by the process provided herein comprises about 10-20% docosapentaenoic acid (C22:5ω6 or DPA) based on total weight of the oil.

The processes provided herein do not use surfactants, including, for example, Polysorbate 80, sodium lauryl sulfate, Dimodan CO-K and others, salts, aggressive chemicals, high temperatures, high pH, drying, and/or harsh mechanical treatment of the fermentation broth.

In one embodiment, the process provided herein comprises the following steps: providing an algae fermentation broth, heating the broth to about 40 to 70° C., adjusting the pH of the broth to about 6 to 9, mixing the broth with an endopeptidase enzyme for about 8-24 hours to obtain a mixture, and extracting the mixture with hexane to obtain the oil high in polyunsaturated fatty acids. In one embodiment, the process provided herein consists essentially of the following steps: providing an algae fermentation broth, heating the broth to about 40 to 70° C., adjusting the pH of the broth to about 6 to 8, mixing the broth with an endopeptidase enzyme for about 8-24 hours to obtain a mixture, and extracting the mixture with hexane to obtain the oil high in polyunsaturated fatty acids.

In one embodiment, the process provided herein comprises the following steps: providing an algae fermentation broth, heating the broth to about 40 to 70° C., adjusting the pH of the broth to about 6 to 9, mixing the broth with a serine endopeptidase enzyme for about 8-24 hours to obtain a mixture, and extracting the mixture with hexane to obtain the oil high in polyunsaturated fatty acids. In one embodiment, the process provided herein consists essentially of the following steps: providing an algae fermentation broth, heating the broth to about 40 to 70° C., adjusting the pH of the broth to about 6 to 8, mixing the broth with a serine endopeptidase enzyme for about 8-24 hours to obtain a mixture, and extracting the mixture with hexane to obtain the oil high in polyunsaturated fatty acids.

In one embodiment, the process provided herein consists of the following steps: providing an algae fermentation broth, heating the broth to about 40 to 70° C., adjusting the pH of the broth to about 6 to 8, mixing the broth with an endopeptidase enzyme for about 8-24 hours to obtain a mixture, and extracting the mixture with hexane to obtain the oil high in polyunsaturated fatty acids.

In one embodiment, the process provided herein consists of the following steps: providing an algae fermentation broth, heating the broth to about 40 to 70° C., adjusting the pH of the broth to about 6 to 8, mixing the broth with a serine endopeptidase enzyme for about 8-24 hours to obtain a mixture, and extracting the mixture with hexane to obtain the oil high in polyunsaturated fatty acids.

In one embodiment, the process provided herein comprises providing an algae fermentation broth, heating the broth to about 50° C., adjusting the pH of the broth to about 7, mixing the broth with an endopeptidase enzyme for about 8-24 hours to obtain a mixture, and extracting the mixture with hexane to obtain the oil high in polyunsaturated fatty acids.

In one embodiment, the process provided herein comprises providing an algae fermentation broth, heating the broth to about 50° C., adjusting the pH of the broth to about 7, mixing the broth with a serine endopeptidase enzyme for about 8-24 hours to obtain a mixture, and extracting the mixture with hexane to obtain the oil high in polyunsaturated fatty acids.

In one embodiment, the process provided herein consists essentially of providing an algae fermentation broth, heating the broth to about 50° C., adjusting the pH of the broth to about 7, mixing the broth with an endopeptidase enzyme for about 8-24 hours to obtain a mixture, and extracting the mixture with hexane to obtain the oil high in polyunsaturated fatty acids.

In one embodiment, the process provided herein consists essentially of providing an algae fermentation broth, heating the broth to about 50° C., adjusting the pH of the broth to about 7, mixing the broth with a serine endopeptidase enzyme for about 8-24 hours to obtain a mixture, and extracting the mixture with hexane to obtain the oil high in polyunsaturated fatty acids.

In one embodiment, the process provided herein consists of providing an algae fermentation broth, heating the broth to about 50° C., adjusting the pH of the broth to about 7, mixing the broth with an endopeptidase enzyme for about 8-24 hours to obtain a mixture, and extracting the mixture with hexane to obtain the oil high in polyunsaturated fatty acids.

In one embodiment, the process provided herein consists of providing an algae fermentation broth, heating the broth to about 50° C., adjusting the pH of the broth to about 7, mixing the broth with a serine endopeptidase enzyme for about 8-24 hours to obtain a mixture, and extracting the mixture with hexane to obtain the oil high in polyunsaturated fatty acids.

In one aspect, the oil recovered from the process provided herein is used in an animal feed, or is further processed from human consumption.

The following examples present certain exemplary embodiments and are intended by way of illustration and not by way of limitation. In each of the examples herein, percentages indicate weight percent of the total mixture, unless otherwise indicated.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of the claimed subject matter. Unless indicated otherwise, temperature is in ° C. or is at ambient temperature, and pressure is at or near atmospheric. There are numerous variations and combinations of reaction conditions, e.g., component concentrations, temperatures, and other reaction ranges and conditions that can be used to optimize the product purity and yield obtained from the described process. Only reasonable and routine experimentation will be required to optimize such process conditions.

The algae fermentation broth used in the examples below has the composition provided in Table 1.

TABLE 1

| *Schizochytrium limacinum* broth | |
|---|---|
| Lipid Profile | |
| % C16:0 | 24.17 |
| % C22:5n6 | 16.69 |
| % C22:6n3 | 54.76 |
| Solids (%) | 18.3 |
| Dry Cell Weight (g/kg) | 174.2 |
| Total Lipids (g/L) | 104.22 |
| Total Solids (g/kg) | 182.9 |
| Total Lipids/Total Solids (%) | 57.0 |

The following equipment was used in the examples below:

Homogenizer: GEA Niro Soavi PandaPlus 2000 at 1200 bar pressure

Ultrasound: Hielscher Ultrasonic homogenizer UP400St (400 W)

Shear mixer: IKA Labor-Pilot 2000/4—rotor/stator (three sets) either "fine" or "super fine"

Centrifuge: Eppendorf centrifuge, model 5810R

Rotary Table: Tecnal model TE421 set at 150 rpm at 50° C.

Bioreactor: Sartorius—Biostat B plus set at 1000 rpm at 50° C.

Overhead Mixer: IKA Works—RW20 digital

Rotary Evaporator: Marconi—MA175 set at 40° C. at 300 mm Hg until condensation stop. Then temperature was increased to 60° C. for 5 minutes for complete evaporation of solvent.

The following enzymes were used in the processes described in the examples below:

Lecitase Ultra—Novozymes—lot number LYN05100 (activity 10 KLU/g)

Alcalase—Novozymes—lot number PLN05467 (activity 2.4 AU-A/g)

Lysozyme—Sigma-Aldrich—lot number SLBQ0509V (activity 40000 U/mg)

Sulfatase—Sigma Aldrich—lot number SLBS3558V (activity 10000 U/mg)

Corolase 7089—AB Enzymes—lot number F152753ST (activity 840 UHb/g)

Maxipro BAP—DSM—lot number 417692701 (activity 480 U/g)

The following extraction methods were used in the examples below:

Ethanol Extraction Method:

An aliquot of 325 grams of treated broth was added to a 1000 ml beaker. 175 ml of 70% ethanol was added to the beaker and the material mixed. The beaker was placed into a 70° C. water bath for 10 minutes. The material was then transferred into a 600 ml beaker and heated with stirring until the ethanol evaporated. The liquid mixture was centrifuged in 50 ml disposable tube at 4000 rpm for 5 minutes and the supernatant oil layer was recovered dried and weighed.

Hexane Extraction Method:

A 25 ml aliquot of treated broth was added to a 50 ml disposable centrifuge tube. 25 ml of hexane was added and the mixture was shaken for approximately 5 minutes at 60° C. The centrifuge tube was placed into a centrifuge and spun for 5 minutes at 4000 rpm. The hexane/oil layer was decanted off into a tared beaker. A second 25 ml aliquot of hexane was added to the centrifuge tube and shaken approximately 20 seconds. The remaining hexane/oil was decanted into the first tared beaker. The hexane was evaporated and the oil was recovered and measured.

Example 1

1 kg aliquots of broth were taken from the fermenter and processed through various mechanical procedures in order to rupture the cells as follows: 1) fed to a homogenizer, 2) fed to a shear mixer via gravity, and 3) mixed by ultrasound for 1 minute, all at 70° C. All of the mechanically treated broths were transformed into fatty emulsions. No change in the mechanically untreated broth was observed. The broths were then extracted using the ethanol procedure describe above.

TABLE 2

| Mechanical treatment for oil recovery | | | | | | |
|---|---|---|---|---|---|---|
| Trial | Equipment | Pressure | Time | Rotors/Stator | Power | Passes | Oil recovered (%) Ethanol |
| 1 | none | — | — | — | — | — | 0 |
| 2 | homogenizer | 1200 bar | — | — | — | 1 | 0 |
| 3 | homogenizer | 1200 bar | — | — | — | 2 | 0 |
| 4 | ultra sound | — | 1 min | — | 20 kHz | | 0 |
| 5 | shear mixer | — | — | fine | 60 Hz | 1 | 0 |
| 6 | shear mixer | — | — | super fine | 60 Hz | 1 | 0 |

No lipids were recovered from the emulsified broth or the untreated broth (no cells were ruptured).

Example 2

1 kg aliquots of broth were taken from the fermenter and placed into 1500 ml Erlenmeyer flasks. The pH of broth in each of the Erlenmeyer flasks was adjusted from 5.5 to 7. A 10 U/g of Lysozyme was prepared by adding 0.025 mg of enzyme into 10 milliliters of water and dissolved. In each trial where Lysozyme was utilized, 1 ml of the prepared enzyme was added to the broth. In each trial where Alcalase was utilized, 2.0 grams of the commercial product were added to the broth (0.2% wt/wt). The trials where Lecitase Ultra was utilized, 20 grams of the commercial product were added to the broth (2% wt/wt). The various enzymes were added to each flask and mixed. The flasks were capped and placed into a 50° C. rotary table overnight to allow the enzyme to react with the broth.

TABLE 3

Mechanical and enzymatically treated broth for oil recovery.

| Trial | Equipment | Pressure | Passes | Enzymes | Oil recovered (%) Ethanol | Hexane |
|---|---|---|---|---|---|---|
| 7 | homogenizer | 1200 bar | 1 | Lysozyme + Alcalase | 0 | — |
| 8 | homogenizer | 1200 bar | 2 | Lysozyme + Alcalase | 0 | — |
| 9 | — | — | — | Lysozyme + Alcalase | 4 | 21 |
| 10 | homogenizer | 1200 bar | 1 | Alcalase | 0 | — |
| 11 | homogenizer | 1200 bar | 2 | Alcalase | 0 | — |
| 12 | — | — | 0 | Alcalase | 5 | 50 |
| 13 | homogenizer | 1200 bar | 1 | Lysozyme + Lecitase Ultra | 0 | — |
| 14 | homogenizer | 1200 bar | 2 | Lysozyme + Lecitase Ultra | 0 | — |
| 15 | — | — | — | Lysozyme + Lecitase Ultra | 0 | — |
| 16 | homogenizer | 1200 bar | 1 | Lysozyme | 0 | — |
| 17 | homogenizer | 1200 bar | 2 | Lysozyme | 0 | — |
| 18 | — | — | — | Lysozyme | 0 | — |

The broth was fed to the homogenizer and shear mixer via gravity. In all of the trials where the homogenizer or the shear mixer were utilized, an emulsion was produced that did not release any oil in either the ethanol or hexane extraction procedures. In the trials where no mechanical treatment was utilized and Alcalase was employed, some of the oil was released from the treated broth.

Example 3

8 kg of broth was heated to 50° C. The pH was raised from 5.5 to 7.0 with dilute sodium hydroxide while mixing 0.3% (wt/wt) ALCALASE® 2.4 L FG. The material was allowed to react overnight. 1 Liter aliquots were taken and run through the shear mixer. Two different extraction methods were carried out. As seen from data in Table 4, the energy inputted by the shear mixer had a negative effect on amount of recovered oil from the enzymatic process.

TABLE 4

| Trial | Speed (Hz) | Rotors/Stator | Oil recovered (%) Ethanol | Hexane |
|---|---|---|---|---|
| 19 | None | — | — | 60.5 | 102.1 |
| 20 | Single Pass | 30 | fine | 39.5 | 100.9 |
| 21 | Single Pass | 60 | fine | 40.0 | 96.7 |

Example 4

The fermentation broth used in Examples 4 and 5 had the following characteristics:

TABLE 5

*Schizochytrium limacinum* broth

| Lipid Profile | B1 | B2 | B3 |
|---|---|---|---|
| % C16:0 | 34.1 | 35.2 | 33.7 |
| % C22:5n6 | 16.3 | 15.9 | 15.3 |
| % C22:6n3 | 45.7 | 45.1 | 47.0 |
| Solids (%) | 17.9 | 17.8 | 18.4 |
| Dry Cell Weight (g/kg) | 170.17 | 174.98 | 176.64 |
| Total Lipids (g/L) | 115.0 | 113.0 | 115.2 |
| Total Solids (g/kg) | 178.99 | 177.82 | 183.75 |
| Total Lipids/Total Solids (%) | 64.27 | 63.52 | 62.69 |

About 500 g aliquots of broth (B2) were taken from the fermenter and placed into 1000 mL beakers. The pH of broth in each of the beakers was adjusted from 5.5 to 6, 7, 8, and 9 with dilute potassium hydroxide while mixing. 0.3% (wt/wt) ALCALASE® 2.4 L FG was added for each of the beakers. About 350 g aliquots from each of the beakers were taken and placed into 1000 Erlenmeyer flasks. The flasks were capped and placed into a 50° C. rotary table overnight to allow the enzyme to react with the broth. About 25 g aliquots were taken for each trial and extracted twice with 25 mL of hexane (total of 50 mL) to recover the oil. For the trial at pH 7, 25 g aliquots were taken also at the times 1, 2, 4, and 8 hours of enzyme reaction for extraction with hexane.

About 2 kg of broth (B2) was taken from the fermenter and placed into a 4000 beaker. The pH was raised from 5.5 to 7.0 with dilute potassium hydroxide while mixing. About 350 g aliquots were taken from the 4000 L beaker and placed into 500 mL beakers.

In the trials that used ALCALASE® 2.4 L FG, 0.1% or 0.2% ALCALASE® 2.4 L FG was added to the broth. In the trial that used Corolase, 0.3% (wt/wt) of Corolase was added to the broth. In the trial used MAXIPRO BAP, 0.3% (wt/wt) of MAXIPRO BAP was added to the broth.

About 350 g aliquots from each of the beakers were taken and placed into 1000 Erlenmeyer flasks. The flasks were capped and placed into a 50° C. rotary table overnight to allow the enzymes to react with the broth. About 25 g aliquots were taken for each trial and extracted twice with 25 mL of hexane (total of 50 mL) to recovery the oil.

About 1 kg of broth (B3) was taken from the fermenter. The pH of broth was adjusted from 5.5 to 7 with dilute potassium hydroxide while mixing. About 0.3% (wt/wt) ALCALASE® 2.4 L FG was added. About 350 g aliquot from beaker was taken and placed into 1000 Erlenmeyer flask. The flask was capped and placed into a 60° C. rotary table overnight to allow the enzyme to react with the broth. 25 g aliquot was taken and extracted twice with 25 mL of hexane (total of 50 mL) to recovery the oil.

About 2 kg of broth (B3) was heated to 70° C. in bioreactors. The pH was raised from 5.5 to 7.0 with dilute potassium hydroxide while mixing. About 0.3% (wt/wt) ALCALASE® 2.4 L FG was added. The material was allowed to react overnight. About 25 g aliquot was taken and extracted twice with 25 mL of hexane (total of 50 mL) to recovery the oil.

About 1 kg of broth (B3) was taken from the fermenter. The pH of broth was adjusted from 5.5 to 7.0 with dilute potassium hydroxide while mixing. About 200 g aliquot was taken and placed into a 1000 mL beaker. About 3.37 mg/L SULFATASE and 10 U/mL LYSOZYME were added. About 200 g aliquot from beaker was taken and placed into 1000 Erlenmeyer flask. The flask was capped and placed into a 60° C. rotary table overnight to allow the enzyme to react with the broth. About 25 g aliquots were taken for each trial and extracted twice with 25 mL of hexane (total of 50 mL) to recover the oil.

TABLE 6

| Trial | Enzyme | pH | Temperature | Enzyme reaction time | Oil recovered (%) |
|---|---|---|---|---|---|
| 25 | Alcalase 0.3% | 6 | 50 | Overnight | 84.3 |
| 26 | Alcalase 0.3% | 7 | 50 | 1 hour | 0 |
| 27 | Alcalase 0.3% | 7 | 50 | 2 hours | 0 |
| 28 | Alcalase 0.3% | 7 | 50 | 4 hours | 0 |
| 29 | Alcalase 0.3% | 7 | 50 | 8 hours | Trace * |
| 30 | Alcalase 0.3% | 7 | 50 | Overnight | 91.2 |
| 31 | Alcalase 0.3% | 8 | 50 | Overnight | 95.6 |
| 32 | Alcalase 0.3% | 9 | 50 | Overnight | 97.7 |
| 33 | Alcalase 0.1% | 7 | 50 | Overnight | 49.2 |
| 34 | Alcalase 0.2% | 7 | 50 | Overnight | 94.0 |
| 35 | Alcalase 0.3% | 7 | 60 | Overnight | 75.0 |
| 36 | Alcalase 0.3% | 7 | 70 | Overnight | 85.1 |
| 37 | Corolase 0.3% | 7 | 50 | Overnight | 0 |
| 38 | Maxipro 0.3% | 7 | 50 | Overnight | 91.3 |
| 39 | Sulfatase 3.37 mg/mL + Lysozyme 10 U/mL | 7 | 50 | Overnight | 0 |

* Trace meaning yellow color of oil present in solvent, but not recovered.

Example 5

About 8 kg of broth (B1) was heated to 50° C. in a bioreactor. The pH was raised from 5.5 to 7.0 with dilute potassium hydroxide while mixing. About 0.3% (wt/wt) ALCALASE® 2.4 L FG was added. The material was allowed to react overnight. About 2 liter aliquots were taken and extracted twice with 250 mL of hexane (total of 500 mL). The hexane was incorporated with the use of an overhead mixer at 250 rpm for 30 minutes. The hexane and oil were separated using 250 mL centrifuge tubes and collected. The hexane was removed from the oil with a rotary evaporator and 760 grams of oil were collected.

About 12 kg of broth (B2) was heated to 50° C. in bioreactors. The pH was raised from 5.5 to 7.0 with dilute potassium hydroxide while mixing. About 0.3% (wt/wt) ALCALASE® 2.4 L FG was added. The material was allowed to react overnight. About 2 liter aliquots were taken and extracted twice with 250 mL of hexane (total of 500 mL). The hexane was incorporated with the use of an overhead mixer at 250 rpm for 30 minutes. The hexane and oil were separated using 250 mL centrifuge tubes and collected. The hexane was removed from the oil with a rotary evaporator and About 1,125 grams of oil were collected.

The two oils were combined (1,875 grams) and washed with 1000 grams of boiling water. The oil was decanted off and dried using the rotary evaporator.

About 12 kg of broth (B2) was heated to 50° C. in bioreactors. The pH was raised from 5.5 to 7.0 with dilute potassium hydroxide while mixing. About 0.3% (wt/wt) ALCALASE® 2.4 L FG was added. The material was allowed to react overnight. 2 liter aliquots were taken and extracted twice with 250 mL of hexane (total of 500 mL). The hexane was incorporated with the use of an overhead mixer at 250 rpm for 30 minutes. The hexane and oil were separated using 250 mL centrifuge tubes and collected. The hexane was removed from the oil with a rotary evaporator and 1,390 grams of oil were collected.

About 12 kg of broth (B3) was heated to 50° C. in bioreactors. The pH was raised from 5.5 to 7.0 with dilute potassium hydroxide while mixing. About 0.3% (wt/wt) ALCALASE® 2.4 L FG was added. The material was allowed to react overnight. About 2 liter aliquots were taken and extracted twice with 250 mL of hexane (total of 500 mL). The hexane was incorporated with the use of an overhead mixer at 250 rpm for 30 minutes. The hexane and oil were separated using 250 mL centrifuge tubes and collected. The hexane was removed from the oil with a rotary evaporator and 1,270 grams of oil were collected.

About 8 kg of broth (B3) was heated to 50° C. in bioreactors. The pH was raised from 5.5 to 7.0 with dilute potassium hydroxide while mixing. About 0.3% (wt/wt) ALCALASE® 2.4 L FG was added. The material was allowed to react overnight. 2 liter aliquots were taken and extracted twice with 250 mL of hexane (total of 500 mL). The hexane was incorporated with the use of an overhead mixer at 250 rpm for 30 minutes. The hexane and oil were separated using 250 mL centrifuge tubes and collected. The hexane was removed from the oil with a rotary evaporator and 670 grams of oil were collected.

TABLE 7

| Fatty Acid Composition of the extracted oil lot 1719026020C4:0 | 0.00 | 0.00 |
|---|---|---|
| C6:0 | 0.00 | 0.00 |
| C8:0 | 0.00 | 0.00 |
| C10:0 | 0.05 | 0.02 |
| C11:0 | 0.00 | 0.00 |
| C12:0 | 0.00 | 0.00 |
| C13:0 | 0.00 | 0.00 |
| C14:0 | 0.64 | 0.71 |
| C14:1 | 0.17 | 0.18 |
| C15:0 | 0.02 | 0.03 |
| C15:1 | 0.00 | 0.00 |
| C16:0 | 31.27 | 30.97 |
| C16:1 | 0.09 | 0.10 |
| C17:0 | 0.00 | 0.00 |
| C17:1 | 0.23 | 0.24 |
| C18:1 | 1.37 | 1.39 |
| C18:2 | 0.02 | 0.03 |
| C18:3n3 | 0.00 | 0.00 |
| C18:3n6 | 0.11 | 0.11 |
| C20:0 | 0.16 | 0.16 |
| C20:1n9 | 0.00 | 0.00 |
| C20:2 | 0.00 | 0.00 |
| C20:3n3 | 0.00 | 0.00 |
| C20:3n6 | 0.00 | 0.02 |
| C20:4n6 | 0.02 | 0.02 |
| C20:5n3 | 0.00 | 0.00 |
| C21:0 | 0.03 | 0.02 |
| C22:0 | 0.09 | 0.10 |
| C22:1n9 | 0.03 | 0.07 |
| C22:2 | 0.00 | 0.00 |
| C22:5n6 | 17.11 | 17.21 |

TABLE 7-continued

| | | |
|---|---|---|
| C22:6n3 | 48.59 | 48.62 |
| C24:0 | 0.00 | 0.00 |
| Other | 0.00 | 0.00 |

| Duplicate analysis of same sample | |
|---|---|
| Free Fatty Acid (% as oleic) | 0.13 |
| Gardner Color | 12 |
| Lovibond Color | 6.2 Red |
| | 70 Yellow |
| Metals (ppm) | |
| Phosphorus | 1.9 |
| Calcium | 29.4 |
| Magnesium | 1.2 |
| Iron | 0.7 |

While exemplary embodiments of the process have been set forth herein, other embodiments encompassing the method will be readily apparent to those skilled in the art, and all such embodiments and their equivalents are intended to be covered by this application and encompassed by the claims hereof.

What is claimed is:

1. A process for extraction of an oil high in polyunsaturated fatty acids from an algae fermentation broth comprising:
contacting the broth with a serine endopeptidase enzyme comprising SEQ ID NO: 1 and extracting the oil high in polyunsaturated fatty acids with a solvent selected from hexane, pentane, heptane and octane, wherein no surfactant is added to the broth, and wherein the algae in the algae fermentation broth is selected from *Thraustochytrium, Schizochytrium* or mixtures thereof.

2. The process of claim 1, wherein the process comprises adjusting the pH of the broth to about 6 to 10.

3. The process of claim 1, wherein the process comprises adjusting the pH of the broth to about 7 to 9.

4. The process of claim 1, wherein the process comprises adjusting the pH of the broth to about 7.

5. The process of claim 1, wherein the process comprises heating the broth to a temperature of about 30° C. to about 80° C.

6. The process of claim 1, wherein the process comprises heating the broth to a temperature of about 50° C.

7. The process of claim 1, wherein the broth is contacted with the serine endopeptidase enzyme for about 8-20 hours.

8. The process of claim 1, wherein the broth is contacted with the serine endopeptidase enzyme for about 8-15 hours.

9. The process of claim 1, wherein the solvent is hexane.

10. The process of claim 1, wherein the algae fermentation broth comprises an algae density of from about 40 to about 250 g/L.

11. The process of claim 1, wherein the algae in the broth comprises about 30% to about 80% oil high in polyunsaturated fatty acids based on the total weight of the algae.

12. The process of claim 1, wherein the algae in the broth comprises about 50% to about 70% oil high in polyunsaturated fatty acids based on the total weight of the algae.

13. The process of claim 1, wherein greater than about 50% oil high in polyunsaturated fatty acids is recovered from the algae fermentation broth based on the total amount of polyunsaturated fatty acid oil present in the algae biomass.

14. The process of claim 1 comprising: providing an algae fermentation broth, heating the broth to about 50° C., adjusting the pH of the broth to about 7, mixing the broth with the serine endopeptidase enzyme for about 8-24 hours to obtain a mixture, and extracting the mixture with hexane to obtain the oil high in polyunsaturated fatty acids.

15. The process claim 1 consisting essentially of: providing an algae fermentation broth, heating the broth to about 50° C., adjusting the pH of the broth to about 7, mixing the broth with the serine endopeptidase enzyme for about 8-24 hours to obtain a mixture, and extracting the mixture with hexane to obtain the oil high in polyunsaturated fatty acids.

16. The process of claim 1, wherein the oil comprises greater than 50%, 60%, 70% or 80% polyunsaturated fatty acids based on total weight of the oil.

17. The process of claim 1, wherein the oil comprises about 45-65% docosahexaenoic acid based on total weight of the oil.

18. The process of claim 1, wherein the oil comprises about 10-25% docosapentaenoic acid based on total weight of the oil.

19. A process for extraction of an oil high in polyunsaturated fatty acids from an algae fermentation broth comprising:
contacting the broth with a serine endopeptidase enzyme from *Bacillus licheniformis* and extracting the oil high in polyunsaturated fatty acids with a solvent selected from hexane, pentane, heptane and octane, wherein no surfactant is added to the broth, the algae in the algae fermentation broth is selected from *Thraustochytrium, Schizochytrium* or mixtures thereof and the serine endopeptidase enzyme comprises SEQ ID NO: 1.

20. The process of claim 1, wherein the algae is *Schizochytrium limacinum*.

21. The process of claim 19, wherein the algae is *Schizochytrium limacinum*.

* * * * *

SEQUENCE LISTING

```
<160> NUMBER OF SEQ ID NOS: 1

<210> SEQ ID NO 1
<211> LENGTH: 30
<212> TYPE: PRT
<213> ORGANISM: Bacillus licheniformis

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30
```